US008845518B2

(12) United States Patent
Oneda et al.

(10) Patent No.: US 8,845,518 B2
(45) Date of Patent: Sep. 30, 2014

(54) INFLATABLE MEMBER FOR AN ENDOSCOPE SHEATH

(75) Inventors: Katsumi Oneda, Alpine, NJ (US); Edward Paul Harhen, Duxbury, MA (US); Mark S. Landman, Sharon, MA (US)

(73) Assignee: Vision Sciences, Inc., Natick, MA (US)

( * ) Notice: Subject to any disclaimer, the term of this patent is extended or adjusted under 35 U.S.C. 154(b) by 1498 days.

(21) Appl. No.: 11/373,453

(22) Filed: Mar. 9, 2006

(65) Prior Publication Data

US 2006/0161044 A1 Jul. 20, 2006

Related U.S. Application Data

(60) Division of application No. 10/094,406, filed on Mar. 8, 2002, now abandoned, which is a continuation-in-part of application No. 09/702,155, filed on Oct. 30, 2000, now Pat. No. 6,461,294.

(51) Int. Cl.
*A61B 1/04* (2006.01)

(52) U.S. Cl.
USPC ........ 600/115; 600/114; 600/121; 604/95.01; 604/95.03

(58) Field of Classification Search
USPC ............... 600/114–116, 121–125; 604/95.03, 604/101.01, 101.05, 103.06, 103.12
See application file for complete search history.

(56) References Cited

U.S. PATENT DOCUMENTS

| 3,776,222 A | 12/1973 | Smiddy | 1/6 |
| 4,066,070 A | 1/1978 | Utsugi | 128/4 |
| 4,148,307 A | 4/1979 | Utsugi | 128/4 |
| 4,176,662 A | 12/1979 | Frazer | 128/6 |
| 4,180,076 A | 12/1979 | Betancourt | 128/349 B |
| 4,207,872 A * | 6/1980 | Meiri et al. | 600/116 |
| 4,224,929 A | 9/1980 | Furihata | 128/5 |
| 4,295,464 A | 10/1981 | Shihata | 128/1 R |
| 4,404,971 A | 9/1983 | LeVeen et al. | 128/348.1 |
| 4,636,195 A * | 1/1987 | Wolinsky | 604/509 |
| 4,676,228 A | 6/1987 | Krasner et al. | 600/116 |

(Continued)

FOREIGN PATENT DOCUMENTS

| JP | 04-236964 | 8/1992 |
| WO | WO 01/72370 | 10/2001 |

OTHER PUBLICATIONS

Response as filed in reply to EP Office Action dated May 17, 2010 regarding Application No. 03711472.5.

(Continued)

*Primary Examiner* — Matthew J Kasztejna
(74) *Attorney, Agent, or Firm* — Dorsey & Whitney LLP (57) ABSTRACT

Apparatus and methods for attaching and forming enclosed inflatable members on an endoscope assembly with a disposable sheath are disclosed. In one embodiment, an apparatus includes a flexible and resilient cuff member that is positioned on the outer surface of the disposable sheath and sealably and fixedly bonded to the sheath cover material at the cuff edges to form an annular space capable of being inflated. The inflatable member formed thereby is inflated through a lumen internal to the sheath that has an opening into the interior annular space. The inflatable member may be inflated to exert a longitudinal force on the insertion tube, thereby moving the endoscope assembly along a body passage. Alternately, a sheath may include a plurality of inflatable cuffs that may be inflated to create an isolated space therebetween within the body passage.

12 Claims, 9 Drawing Sheets

(56) References Cited

U.S. PATENT DOCUMENTS

| | | | |
|---|---|---|---|
| 4,690,131 A | 9/1987 | Lyddy, Jr. et al. | 128/4 |
| 4,752,286 A | 6/1988 | Okada | 604/96 |
| 4,836,024 A * | 6/1989 | Woehrl et al. | 307/10.1 |
| 4,836,204 A * | 6/1989 | Landymore et al. | 606/215 |
| 4,838,859 A * | 6/1989 | Strassmann | 604/95.03 |
| 4,892,099 A | 1/1990 | Ohkawa et al. | 606/194 |
| 4,934,786 A * | 6/1990 | Krauter | 385/118 |
| 4,947,827 A | 8/1990 | Opie et al. | 600/108 |
| 4,976,261 A | 12/1990 | Gluck et al. | 128/207.15 |
| 5,025,778 A | 6/1991 | Silverstein et al. | 600/104 |
| 5,078,681 A | 1/1992 | Kawashima | 606/198 |
| 5,090,259 A * | 2/1992 | Shishido et al. | 73/866.5 |
| 5,152,277 A | 10/1992 | Honda et al. | 128/4 |
| 5,217,001 A | 6/1993 | Nakao et al. | 600/123 |
| 5,304,132 A * | 4/1994 | Jang | 604/101.01 |
| 5,331,947 A | 7/1994 | Shturman | 600/115 |
| 5,337,732 A | 8/1994 | Grundfest et al. | 600/116 |
| 5,400,770 A | 3/1995 | Nakao et al. | 606/116 |
| 5,419,310 A | 5/1995 | Frassica et al. | 128/4 |
| 5,425,738 A | 6/1995 | Gustafson et al. | 606/153 |
| 5,454,364 A | 10/1995 | Kruger | 600/114 |
| 5,489,256 A | 2/1996 | Adair | 600/113 |
| 5,569,161 A | 10/1996 | Ebling et al. | 600/121 |
| 5,577,992 A | 11/1996 | Chiba et al. | 600/152 |
| 5,628,753 A | 5/1997 | Cracauer et al. | 606/108 |
| 5,645,519 A | 7/1997 | Lee et al. | 600/114 |
| 5,681,342 A | 10/1997 | Benchetrit | 606/192 |
| 5,743,851 A | 4/1998 | Moll et al. | 600/204 |
| 5,749,357 A | 5/1998 | Linder | 128/200.26 |
| 5,810,790 A | 9/1998 | Ebling et al. | 604/523 |
| 5,840,013 A | 11/1998 | Lee et al. | 600/114 |
| 5,876,329 A | 3/1999 | Harhen | 600/125 |
| 5,938,585 A | 8/1999 | Donofrio | 600/115 |
| 6,007,482 A | 12/1999 | Madni et al. | 600/115 |
| 6,060,454 A | 5/2000 | Duhaylongsod | 514/26 |
| 6,086,528 A | 7/2000 | Adair | 600/104 |
| 6,214,022 B1 | 4/2001 | Taylor et al. | 606/153 |
| 6,234,958 B1 | 5/2001 | Snoke et al. | 600/114 |
| 6,234,995 B1 * | 5/2001 | Peacock, III | 604/96.01 |
| 6,277,137 B1 | 8/2001 | Chin | 606/190 |
| 6,315,715 B1 | 11/2001 | Taylor et al. | 600/140 |
| 6,344,028 B1 | 2/2002 | Barry | 604/96.01 |
| 6,461,294 B1 | 10/2002 | Oneda et al. | 600/116 |
| 6,488,653 B1 * | 12/2002 | Lombardo | 604/103.06 |
| 6,585,639 B1 | 7/2003 | Kotmel et al. | 600/116 |
| 6,605,030 B2 * | 8/2003 | Weinberger | 600/3 |
| 6,793,661 B2 | 9/2004 | Hamilton et al. | 606/116 |

OTHER PUBLICATIONS

EP Office Action dated May 17, 2010 regarding Application No. 03711472.5.

EP Office Action dated Nov. 3, 2011 regarding Application No. 03711472.5.

* cited by examiner

INFLATABLE MEMBER FOR AN ENDOSCOPE SHEATH

CROSS-REFERENCE TO RELATED APPLICATIONS

This application is a division of pending U.S. patent application Ser. No. 10/094,406, filed Mar. 8, 2002; which is a continuation-in-part of U.S. patent application Ser. No. 09/702,155, filed Oct. 30, 2002, issued as U.S. Pat. No. 6,461, 294.

TECHNICAL FIELD

This invention relates generally to endoscopy, and more particularly to inflatable members attached to an endoscopic instrument.

BACKGROUND OF THE INVENTION

The use of endoscopes for diagnostic and therapeutic purposes is widespread. For example, there are upper endoscopes for examination of the esophagus, stomach and duodenum, colonoscopes for the examination of the colon, angioscopes for vascular examination, bronchoscopes for examining the bronchi, laparoscopes for examining the peritoneal cavity, and arthroscopes for the examination of joint spaces. The following discussion applies to all of these types of endoscopes.

An endoscope for examining the bronchial tract and conducting transbronchial biopsies is a good example of the usefulness of endoscopic technology. These devices, known as flexible bronchoscopes, are widely used in diagnosing pulmonary diseases since they are capable of reaching the more distal bronchi in the bronchial tract. To properly navigate and view a bronchial area, the bronchoscope is generally structured to contain a fiber optic bundle within the elongated probe section. Alternatively, the bronchoscope may utilize other means to view the bronchial area, such as a video device positioned within the bronchoscope. In addition to providing a direct viewing capability, flexible bronchoscopes generally possess a means to remove tissue samples, or other material from the bronchial tract for biopsy or culture purposes. Tissue samples for biopsy purposes may be collected using a biopsy forceps extending from the distal end of the bronchoscope or by brushing the suspect area to capture cellular material for subsequent microscopic examination. Another commonly used technique to collect cellular material is to wash, or lavage, the suspect area. When a lavage procedure is used, a solution is injected into the bronchial passage and subsequently withdrawn by suction through the distal end of the broncoscope to capture cellular material. Following withdrawal of the lavage fluid, the cellular material may be subjected to a cytological examination or culture.

One difficulty encountered in the use of endoscopes is continuously maintaining the endoscopic probe in a selected location within a body passage during the examination. Movement of the endoscopic probe while it is positioned within a body passage may occur for a number of reasons. For example, movement of the endoscope may occur due to an unintended bodily movement of the operator while the patient is undergoing the examination, or by an involuntary movement of the patient in response to the examination. Once the distal end of the endoscope has been dislodged from its intended location, it must be carefully repositioned before the examination may be resumed. Movement of the endoscope within a body passage is particularly pronounced during bronchoscopic examinations, since the patient must continue to breathe during the examination. Further, involuntary bronchospasmodic events within the bronchial passages may occur during the examination that will disrupt the location of the distal end of the bronchoscope. A significant additional difficulty resulting from unintended patient movement may arise when a biopsy procedure is conducted. Since a biopsy forceps or brush is generally used, an uncontrolled or unintended cutting of tissue in the passage due to patient movement may lead to hemoptysis. Moreover, since the biopsy forceps, or brush may reach and perforate the pleura, pneumothorax may also occur.

Still another difficulty encountered in the use of endoscopes for diagnostic purposes is the inability to sealably isolate a portion of the endoscope from the remainder of the body passage during an endoscopic examination. To facilitate internal viewing of a passage, for example, the fluid occupying the cavity is generally removed by means of a suction channel in the endoscope, which may be followed by the introduction of a gas through an additional channel in the endoscope to distend the internal space. Other endoscopic applications may require that a fluid be retained within the portion of the body passage that has been sealably isolated. For example, in transbronchial diagnostic procedures such as bronchoalveolar lavage, the bronchoscope is used to gently irrigate the air spaces in a distal air passage with a solution. Isolation of the solution to the region surrounding the distal end of the bronchoscope is required so that cellular samples removed during the lavage are sufficiently localized to be of diagnostic value. In particular, when collecting samples by lavage for use in the diagnosis of infectious pulmonary diseases, the sample must not be contaminated by bacterial or other agents transported to the distal end of the probe by the unrestrained movement of the solution through the passage.

Yet another difficulty encountered in the use of endoscopes occurs when the endoscope must be positioned at a relatively deep location within a body passage, so that a relatively long portion of the endoscope must be inserted into the patient. In such cases, the endoscope may be resistant to small, or incremental movements within the passage. Moreover, in certain cases, the endoscope length may develop sufficient resistance to further inward movement, so that the endoscope is prevented from extending to the intended location. Similar difficulties may also occur when the passage is relatively short, but includes relatively highly curved segments. Since the operator is generally limited to positional manipulations of exposed portions of the endoscope, considerable difficulty may be encountered in properly positioning the endoscope within body passages under these conditions.

Increasingly, endoscopes are used with disposable sheaths that are positioned over the insertion tube of the endoscope to avoid the communication of disease from one patient to another. An additional advantage of the disposable sheath is that it allows the device to be used at more frequent intervals, since the need for lengthy cleaning and sterilization procedures is largely eliminated. Generally, the sheath is comprised of a flexible, thin, resilient material, such as latex, or other similar materials, that fits over and surrounds the insertion tube of the endoscope so the insertion tube is completely isolated from contaminants. The sheath is generally further comprised of a viewing window at the distal end, and may include a plurality of internal channels, or lumens, through which biopsy samples or fluids may be either introduced or removed. Accordingly, an additional difficulty encountered in the use of endoscopes concerns the incorporation of positioning and passage-blocking means into the disposable outer sheath.

Consequently, there exists a need in the art for an apparatus that will continuously maintain an endoscopic probe in a selected position within a body passage during the examination. In addition, the apparatus must be able to sealably close the passage to either retain fluids within a closed space, or to prevent a fluid from reoccupying the space during an examination. Further, there exists a need in the art for an apparatus that permits an endoscopic probe to be properly positioned within a long body passage, and/or where the passage is highly curved. Finally, the apparatus must be compatible with disposable sheaths used with endoscopes.

SUMMARY OF THE INVENTION

The invention is directed towards apparatus and methods for attaching and forming enclosed inflatable members on an endoscope assembly with a disposable sheath. In one aspect, an apparatus in accordance with the invention includes a flexible and resilient cuff member that is positioned on the outer surface of the disposable sheath and sealably and fixedly bonded to the sheath cover material at the cuff edges to form an annular space capable of inflation. The inflatable member formed thereby is inflated through a lumen internal to the sheath that has an opening into the interior annular space. In another aspect, the annular space may be divided into separate inflatable lobes. In still another aspect, the cuff member is a flexible and resilient enclosed member that is substantially toroidal in shape that is positioned on the outer surface of the sheath. In a further aspect, the inflatable member is formed from an excess length of sheath cover material disposed on the disposable sheath. A single reentrant fold of sheath material is formed with an edge that is sealably and fixedly bonded to the sheath cover material to form an annular space capable of inflation. In still another aspect, the excess length of cover material may be used to form members with dual reentrant folds that comprise inflatable members with single and dual inflatable lobes. In another aspect, at least a pair of enclosed inflatable members are spaced apart along the sheath of an endoscope insertion tube, which has a plurality of openings that project through the sheath to communicate a fluid to the space formed between the inflatable members. In still another aspect, at least a single enclosed inflatable member that has a first portion capable of a first expansion when inflated, and a second portion capable of a second expansion when inflated, is positioned on an endoscope sheath of an insertion tube to assist in the movement of the endoscope along a body passage.

DETAILED DESCRIPTION OF THE INVENTION

The present invention is generally directed to inflatable members attached to an endoscope. Many of the specific details of certain embodiments of the invention are set forth in the following description and in FIGS. 1 through 15 to provide a thorough understanding of such embodiments. One skilled in the art will understand, however, that the present invention may have additional embodiments, or that the present invention may be practiced without several of the details described in the following description.

In the drawings, like reference numbers identify similar elements or steps. Further, it is understood that the inflatable members depicted in FIGS. 1 through 14 may assume a variety of sizes and shapes that depend on the amount of internal pressurization and/or the internal shape of a body cavity. Accordingly, for clarity of illustration, and to properly illustrate internal features of the various embodiments illustrated in FIGS. 1 through 14, the embodiments are shown at a generally intermediate stage of inflation.

Figure 1:
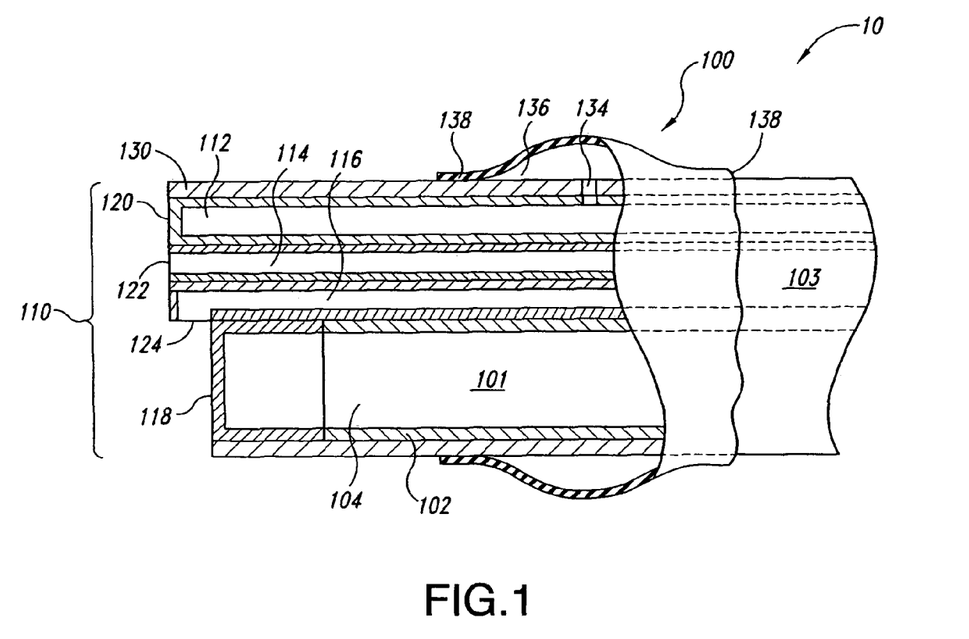
FIG. 1 is a partial cross-sectional view of an endoscope assembly with an inflatable cuff according to an embodiment of the invention.

FIG. 1 is a partial cross sectional view of an endoscope assembly 10 that includes a sheath 103 having an inflatable cuff 100 in accordance with an embodiment of the invention. In this embodiment, the inflatable cuff 100 is circumferentially disposed about a body portion of the sheath 103, the body portion being sized to at least partially encapsulate an insertion tube 101 of an endoscope of the type shown, for example, in FIG. 11.

Figure 15:
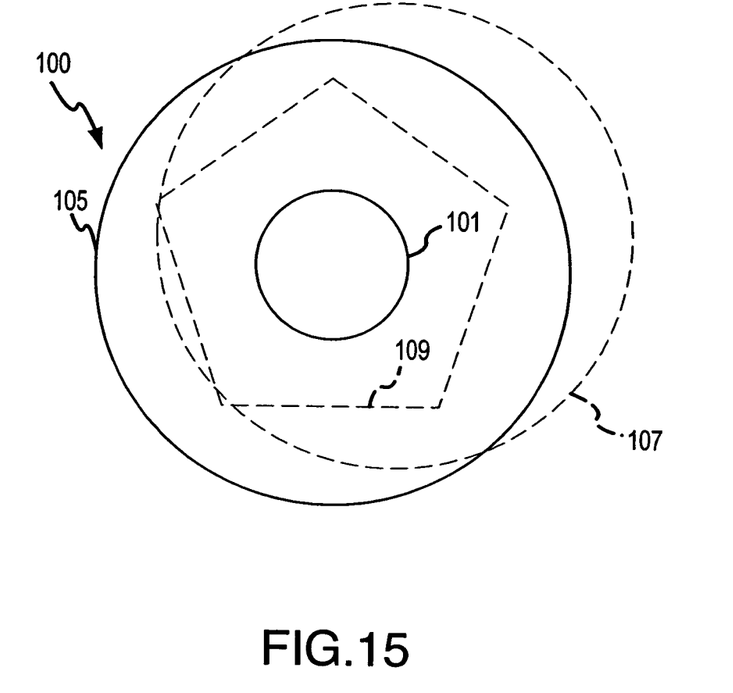
FIG. 15 is an end elevational view of the endoscope assembly of FIG. 1 with the inflatable cuff in the inflated position.

When inflated, the cuff 100 may be symmetrically or asymmetrically disposed about the insertion tube 101. For example, FIG. 15 is an end elevational view of the endoscope assembly 10 with the inflatable cuff 100 shown in an inflated position 105. As shown in FIG. 15, in this embodiment, the inflatable cuff 100 is symmetrically circumferentially disposed about the insertion tube 101. In alternate embodiments, the inflatable cuff 100 may assume any desired shape, including, for example, an eccentrically-disposed circular shape 107 (FIG. 15) that is not symmetrically disposed about the insertion tube 101, or a non-circular, asymmetric shape 109 (FIG. 15), or any other suitable shape.

The insertion tube 101 can have a variety of cross section shapes, such as circular, semicircular, etc., and is fabricated from a resilient material so that an insertion tube wall 102 may be flexed. The insertion tube 101 also has an internal space 104 that is structured to permit the illumination of tissue in internal passages, and to convey an image of the illuminated area from the distal end 110 of the endoscope to an external viewing device (not shown).

With reference still to FIG. 1, the endoscope sheath 103 has a transparent viewing window 118 located at the distal end 110 of the disposable sheath 103 to allow the image to be conveyed to the external viewing device. The window 118 may also be comprised of a lens capable of focusing an image on an image sensing device. The sheath 103 also has a plurality of internal lumens to accomplish specific tasks. For example, a lumen 124 may be provided to direct a flow of rinse water over the viewing window 118 in order to rinse vision-impairing matter from the window 118. A lumen 122 that is open at the distal end 110 may be used to capture a biopsy sample taken from the surrounding tissue area by means of an elongated forceps, or brush (not shown). Alternatively, the lumen 122 may be used to transfer a solution into a body passage during a lavage procedure. Further, the lumen 122 may also be used to transfer a compressed gas into a body passage in order to distend the passage for better optical viewing or biopsy sampling. An additional lumen 120 that is in fluid communication with a pressurized fluid source (not shown) is used to inflate an inflatable endoscope cuff 100, which will be described in greater detail below. The internal lumens 120, 122 and 124 are comprised of a resilient material to maintain flexibility of the sheath 103. The sheath 103 is covered with a flexible, resilient cover material 130 such as latex, polyvinylchloride, or polyurethane. Alternatively, other equally suitable materials for the cover material 130 are KRATON®, available from the GLS Corporation of McHenry, Ill., and C-FLEX®, available from Consolidated Polymer Technologies, Inc. of Largo, Fla.

Still referring to FIG. 1, the inflatable endoscope cuff 100 is comprised of a circular member positioned on the outer surface of the sheath 103. Although only a single inflatable cuff 100 is shown for clarity of illustration, it is understood that a plurality of cuffs 100 may be positioned along the length of the endoscope assembly 10, and that the plurality of cuffs 100 may be positioned at varying relative distances. The inflatable cuff 100 may be located at any location along the working length of the endoscope assembly 10, and forms a closed annular space 136 that is capable of inflation by a pressurized fluid. An opening 134 projects through the cover material 130 and through the wall of the lumen 120 to permit the pressurized fluid retained within the lumen 120 to enter the inflatable cuff 100. To retain the cuff 100 on the surface of the sheath 103, and to retain the pressurized fluid within the annular space 136, the cuff 100 is sealably fastened to the surface of the sheath 103 at the cuff edges 138 with a suitable adhesive placed between the cuff edge 138 and the cover material 130. An example of a suitable adhesive is cyanoacrylate, although other equivalent adhesives exist. Alternatively, the cuff edges 138 may be joined to the cover material 130 either by thermally fusing the cuff edges 138 to the cover material 130, or by wrapping lengths of a retaining cord 131, such as a surgical-type thread or other suitable material, over the cuff edge 138 and securely tying the ends to sealably fasten the cuff edges 138 to the cover material 130, although other methods for attaching the cuff edges 138 to the cover material 130 may also be used.

The inflatable cuff 100 may be formed from latex, KRATON®, or C-FLEX®, although other suitable flexible and resilient materials may be used. For example, soft polyurethane may also be used. Preferably, the inflatable cuff 100 is formed from a flexible and resilient material with a thickness that ranges between 0.003 and 0.010 inches, with a durometer value of between approximately 30 and approximately 50. Alternatively, the cuff 100 may also be formed from a relatively inelastic material, so that it exhibits a relatively baggy shape when not inflated.

Figure 2:
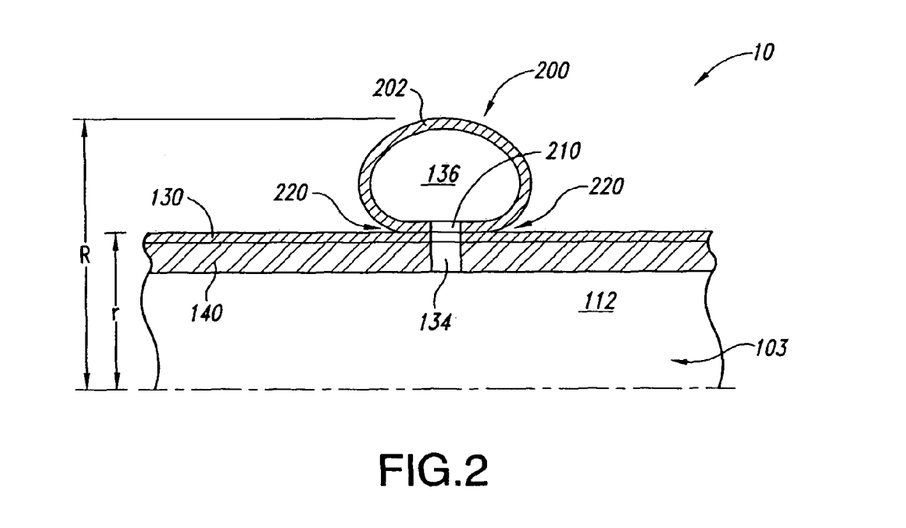
FIG. 2 is a cross-sectional view of an inflatable cuff according to another embodiment of the invention.

With reference now to FIG. 2, a partial cross sectional view of the endoscope assembly 10 with an alternative embodiment of an inflatable endoscope cuff 200 is shown. As shown therein, the inflatable endoscope cuff 200 is comprised of a resilient toroidally-shaped member 202 with an internal radius r and an external radius R. An opening 134 projects through the cover material 130 and through the wall of the lumen 140 to permit a pressurized fluid retained within the lumen interior space 112 to enter the inflatable member 202 through an opening 210 in the interior diameter of the member 202. To sealably retain the pressurized fluid within the annular space 136, the toroidally-shaped member 202 is sealably fastened to the surface of the sheath 103 at a location that is closely proximate to the opening 134. Moreover, to positionally retain the member 202 in the desired location on the surface of the sheath 103, it is preferable to join the interior diameter of the member 202 to the cover material 130 along a circumferential contact area 220 to ensure that the member 202 maintains its position on the endoscope assembly 10.

Figure 3:
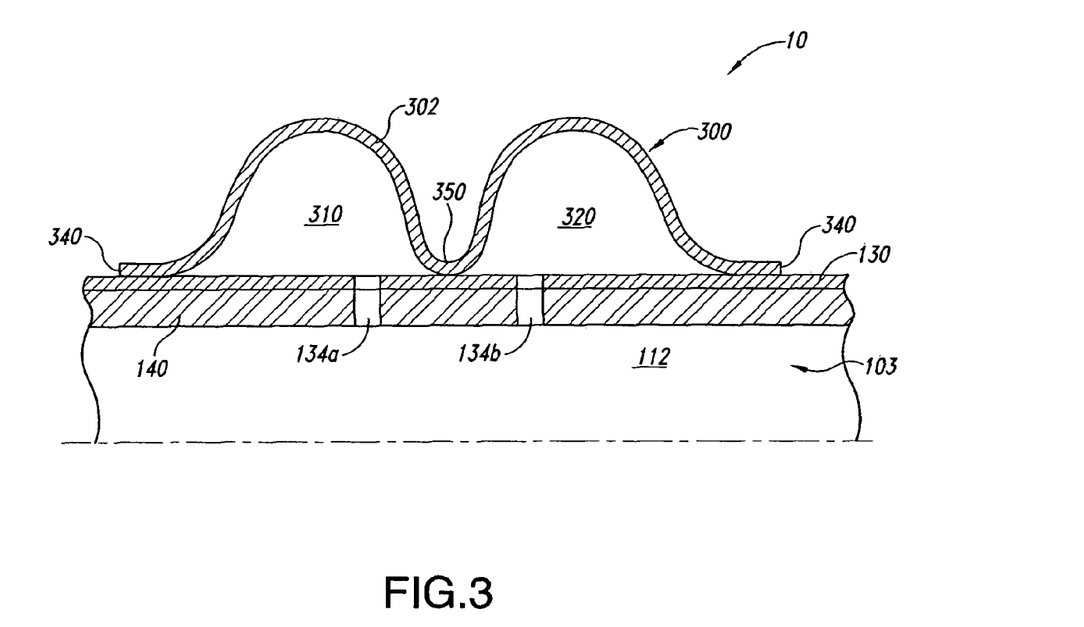
FIG. 3 is a cross-sectional view of an inflatable cuff according to still another embodiment of the invention.

FIG. 3 shows a partial cross sectional view of the endoscope assembly 10 with still another alternative embodiment of an inflatable endoscope cuff 300. As shown in FIG. 3, the inflatable endoscope cuff 300 is comprised of a resilient circular member 302 positioned on the outer surface of the sheath 103. In this embodiment, the length of the endoscope cuff 300 is sufficient to allow the formation of a pair of inflatable annular lobes 310 and 320 by attaching the circular member 302 to the cover material 130 at an approximate midpoint location 350 of the cuff 300. The development of an inflatable endoscope member with dual lobes is regarded as particularly advantageous since the dual lobes are regarded as more effective in conforming to irregular internal surfaces in body passages.

Still referring to FIG. 3, the cuff 300 may be retained at the midpoint location 350, and may be adhesively or thermally bonded to the cover material 130. Alternatively, the cuff may be attached to the cover material 130 at the mid point location 350 by a length of thread 131 (as shown in FIG. 1) wrapped around the cuff 300 that is securely knotted, although other methods may also be used. To retain the pressurized fluid within the inflatable annular lobes 310 and 320, cuff edges 340 are sealably joined to the cover material 130 using an adhesive or thermal bonding method as previously described. Openings 134a and 134b project through the cover material 130 and through the lumen wall 140 to permit the pressurized fluid retained in the lumen interior space 112 to enter the lobes 310 and 320 during inflation.

Figure 4:
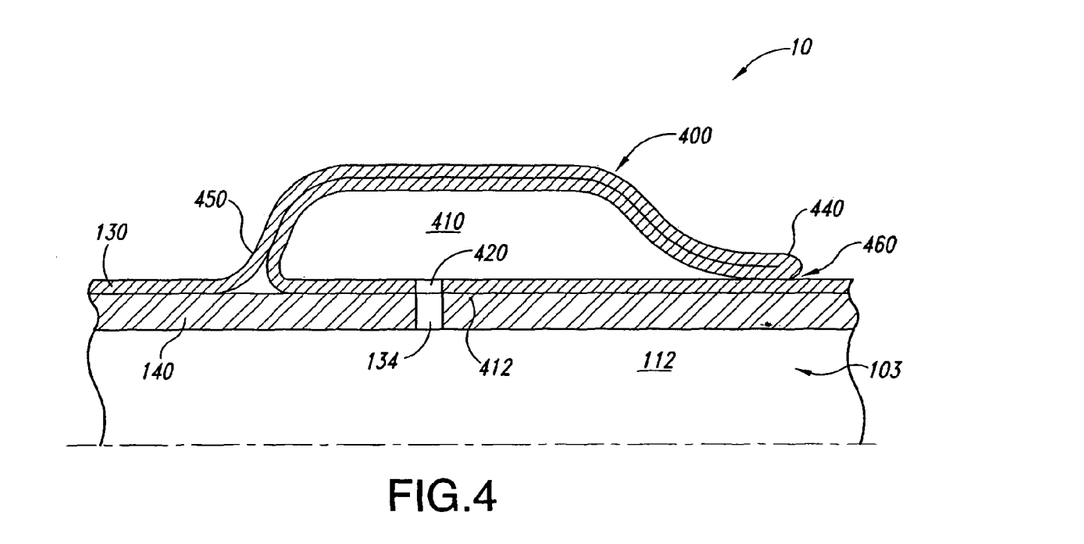
FIG. 4 is a cross-sectional view of an inflatable cuff according to yet another embodiment of the invention.

Turning now to FIG. 4, a partial cross sectional view of the endoscope assembly 10 with yet another alternative embodiment of an inflatable endoscope member 400 is shown. The endoscope assembly 10 according to this embodiment advantageously allows an inflatable member to be formed on the disposable sheath 103 without placing a separate circumferential member on the disposable sheath 103. The inflatable member 400 is formed by providing an excess length of the cover material 130 on the sheath 103 that may be drawn along the surface of the sheath 103 by an edge fold 440 that extends circumferentially around the sheath 103 to form a reentrant fold 450 in the cover material 130 that also extends circumferentially around the disposable sheath 103. The edge fold 440 is subsequently sealably attached to the cover material 130 at a surface location 460 to form a closed annular space 410 that is capable of being inflated. The sealable attachment between the edge fold 440 and the cover material 130 may be comprised of an adhesive or thermal bond. Alternatively, the attachment may be comprised of a length of retaining cord 131 (e.g. surgical-type thread, as shown in FIG. 1) that is wrapped over the edge fold 440 and securely knotted, although other methods may also be used. An opening 420 projects through the cover material 130 and is aligned with the opening 134 through the wall of the lumen 140 to permit the pressurized fluid retained within the lumen interior space 112 to enter the inflatable annular member 400 during inflation. The member 400 may be sealably fastened to the surface of the sheath 103 at a location 412 that is closely proximate to the opening 134 to ensure that the lumen opening 134 in the lumen wall 140 remains in substantial alignment with the opening 420 through the cover material 130.

Figure 5:
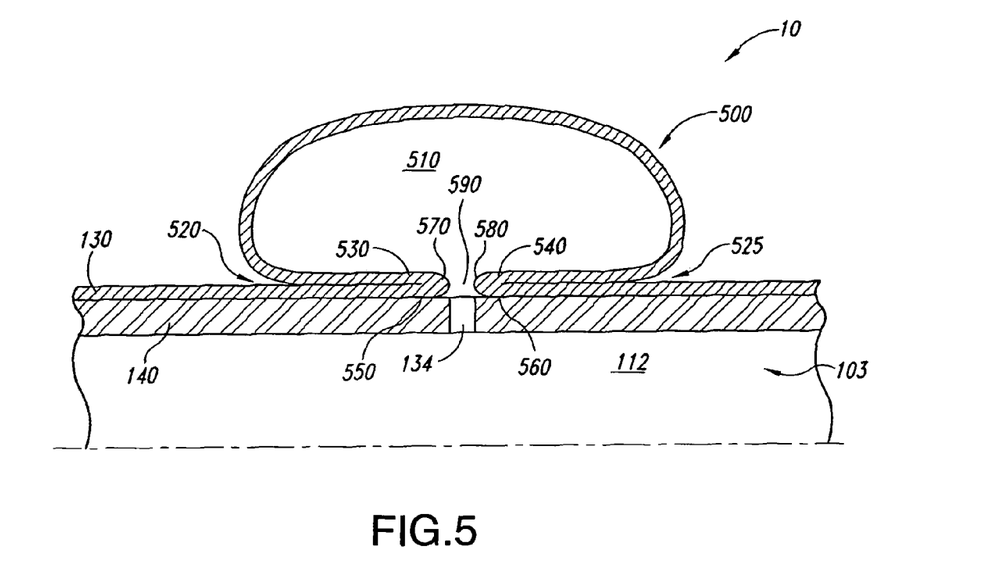
FIG. 5 is a cross-sectional view of an inflatable cuff according to another alternative embodiment of the invention.

FIG. 5 shows a partial cross sectional view of the endoscope assembly 10 with still another alternative embodiment of an inflatable endoscope member 500. As in the previous embodiment, the inflatable endoscope member 500 is advantageously formed from an excess length of the cover material 130 that is disposed on the sheath 103. As shown in FIG. 5, the excess length of the cover material 130 is drawn in a first direction along the surface of the sheath 103 to form a first reentrant fold 530 with a first edge fold 570. The first edge fold 570 is positioned approximately adjacent to the lumen opening 134. A second reentrant fold 540 is then formed in the cover material 130 by drawing the excess length in a second direction that is opposite to the first, to form a second edge fold 580 that is also positioned approximately adjacent to the lumen opening 134. When positioned approximately adjacent to the opening, the first edge fold 570 and the second edge fold 580 form an opening 590 into the inflatable enclosed annular space 510. The first and second reentrant folds 530 and 540 are sealably attached to the lumen wall 140 at locations 550 and 560, respectively, to ensure that the lumen opening 134 remains in substantial alignment with the opening 590. Adhesive or thermal bonding may form the sealable attachment at locations 550 and 560. As an alternative, a retaining cord 131 (e.g. surgical-type thread, as shown in FIG. 1) may be inserted into the first reentrant fold 530 through the opening 520 and also inserted into the second reentrant fold 540 through the opening 525, both lengths of retaining cord being wrapped around the circumference of the disposable sheath 103 and securely knotted to retain the inflatable member 500 in position on the sheath 103, although other methods may also be used.

Figure 6:
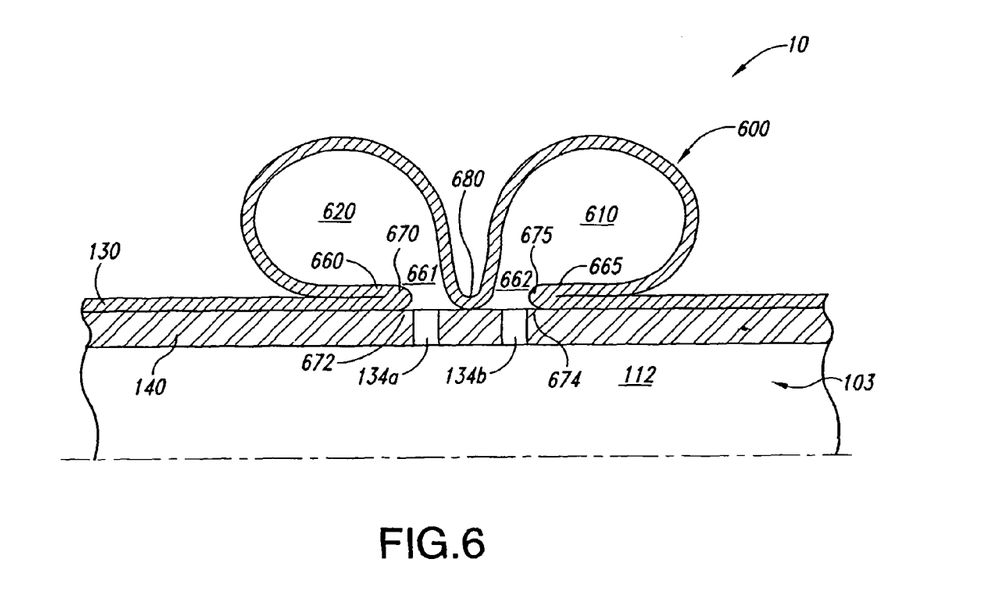
FIG. 6 is a cross-sectional view of an inflatable cuff according to still another alternative embodiment of the invention.

Turning now to FIG. 6, a partial cross sectional view of the endoscope assembly 10 with still another alternative embodiment of an inflatable endoscope member 600 is shown. The inflatable endoscope member 600 is similarly advantageously formed from an excess length of the cover material 130 that is disposed on the sheath 103. Drawing the excess length of cover material 130 along the surface of the sheath 103 in a first direction to form a first reentrant fold 660 with a first edge fold 670 forms the inflatable member 600. The first edge fold 670 is then positioned approximately adjacent to the opening 134a. Drawing the excess length in a second direction that is opposite to the first direction then forms a second reentrant fold 665 with a second edge fold 675. The second edge fold 675 is similarly positioned approximately adjacent to the opening 134b. The inflatable member 600 is divided into a pair of inflatable lobes 610 and 620 by attaching the cover material comprising the member 600 to the lumen wall 140 at an approximate midpoint location 680. The inflatable lobes 610 and 620 are inflated when pressurized fluid retained within the lumen interior space 112 enters the lobes through openings 134a and 134b. The first and second reentrant folds 660 and 665 are sealably attached to the lumen wall 140 at locations 672 and 674 to ensure that the lumen openings 134a and 134b remain in substantial alignment with the lobe entrances 661 and 662. As previously described, adhesive or thermal bonding may be used to form the sealable attachment at locations 672, 674 and 680. As an alternative, a retaining cord 131 may be used to retain the position of the inflatable member on the sheath 103, although other methods may also be used.

Figure 7:
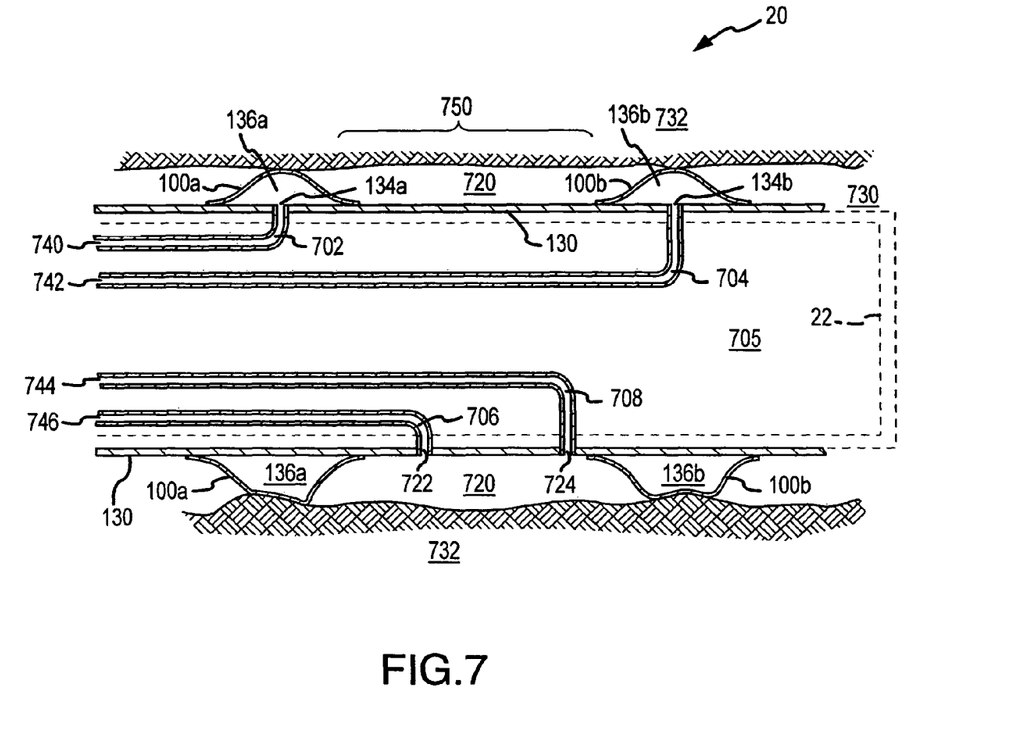
FIG. 7 is a cross-sectional view of an endoscope assembly with inflatable cuffs according to another embodiment of the invention.

FIG. 7 is a cross-sectional view of an endoscope assembly 20 in accordance with yet another alternative embodiment of the invention. The assembly 20 is comprised of a pair of flexible, resilient inflatable cuffs 100a and 100b that are positioned on an outer surface of a disposable sheath 130. The cuffs 100a and 100b are spaced apart along the length of the endoscope assembly 20 to define an inter-cuff length 750. The sheath 130 encloses an interior space 705, and may be positioned on an insertion tube 22 of an endoscope 21 of the type shown, for example, in FIG. 11.

Figure 11:
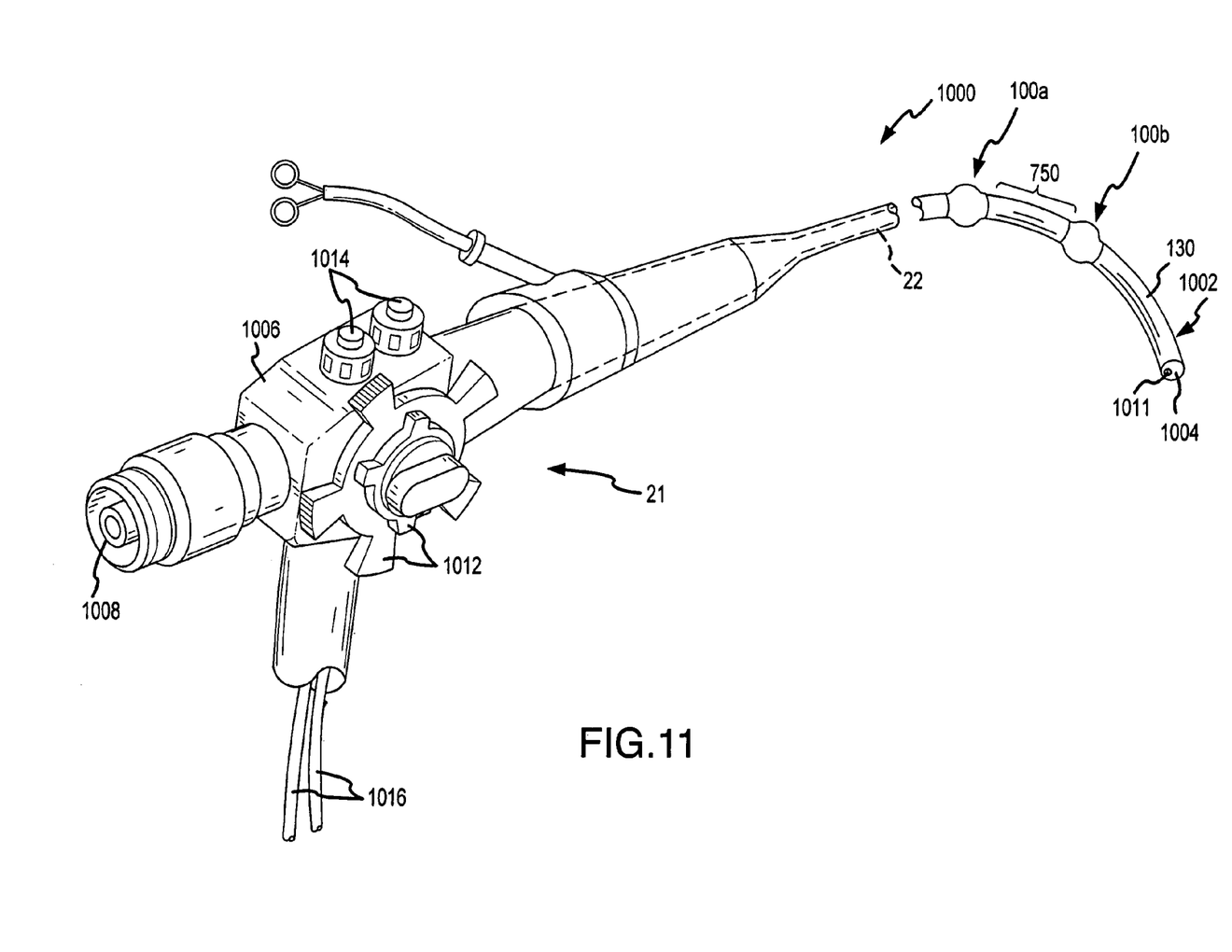
FIG. 11 is an isometric view of an endoscope assembly with inflatable cuffs according to yet another embodiment of the invention.

Referring now to FIG. 11, an endoscope assembly 1000 according to an embodiment of the invention is shown. The endoscope assembly 1000 includes an endoscope 21 having an elongated insertion tube 22 that is comprised of a resilient material so that the tube may be flexed as it is positioned within an internal body passage 730. The insertion tube 22 may be rigid, partially flexible or entirely flexible. The insertion tube 22 includes a distal portion 1002 that may be inserted into a body cavity of a patient (not shown) and a working end 1004. The endoscope 21 includes a headpiece 1006 that remains external to the patient during an endoscopic procedure. In the embodiment shown in FIG. 11, the headpiece 1006 includes an eyepiece 1008 for viewing the scene through a viewing lens 1011 at the working end 1004 of the insertion tube 22, a pair of bending control knobs 1012 for manipulating the position of the distal portion 1002 of the insertion tube 22, and a pair of fluid control actuators 1014 for controlling the flow of fluids through tubes 1016 to (or from) the working end 1002. Endoscopes 21 of the type generally shown in FIG. 11 are described more fully, for example, in U.S. Pat. No. 5,931,833 to Silverstein, U.S. Pat. No. 5,483,951 to Frassica and Ailinger, and U.S. Pat. No. 4,714,075 to Krauter and Vivenzio, which patents are incorporated herein by reference.

Referring now to FIGS. 7 and 11, the sheath 130 shows a pair of inflatable cuffs 100a and 100b. It is understood, however, that the sheath 130 may include a plurality of inflatable cuffs located along the length of the sheath 130, and that the inflatable cuffs may be positioned along the length of the sheath 130 at varying inter-cuff lengths 750. Further, the inflatable cuffs positioned along the length of the sheath 130 may be comprised of any of the inflatable cuffs previously shown in FIGS. 2 through 6. Moreover, any combination of the inflatable cuffs previously shown in FIGS. 2 through 6 may be positioned along the length of the sheath 130.

Referring again to FIG. 7, inflation lumens 702 and 704 are positioned within the interior space 705 of the endoscope 20. The inflation lumens 702 and 704 are fluidly connected to a source of an inflation fluid (not shown) at lumen ends 740 and 742. The lumens 702 and 704 fluidly communicate through openings 134a and 134b to allow the inflation fluid to be separately and selectively introduced into the annular spaces 136a and 136b. In alternate embodiments, the pair of lumens 702 and 704 may be replaced with a single lumen to provide inflation fluid to more than a single inflatable cuff on the endoscope assembly 20, so that the cuffs may be simultaneously inflated. Inflation of the cuffs 100a and 100b through the inflation lumens 702 and 704 thus allows an isolated body space 720 to be formed within the inter-cuff length 750 by sealably impressing the cuffs 100a and 100b against the body passage walls 732 of the body passage 730, as shown, for example, in the lower portion of FIG. 7.

Lumens 706 and 708 may optionally be provided within the interior space 705 that communicate through openings 722 and 724 into the inter-cuff length 750. The lumens 706 and 708 may be fluidly connected to a variety of fluid or suction sources at the opposing ends 744 and 746 in order to accomplish a variety of diagnostic tasks. For example, the lumen 706 may be fluidly connected to a source of a solution (not shown) to introduce the solution into the isolated body space 720. The solution may then be subsequently withdrawn from the space 720 through another lumen 708 for analysis. Alternatively, the lumen 706 may be fluidly connected to a source of pressurized fluid (not shown) that may be used to distend the isolated body space 720 prior to the introduction of a solution into the space 720 by the lumen 708. Although a pair of lumens 706 and 708 is shown in FIG. 7, it is understood that a single lumen, or more than two may optionally be used.

The endoscope assembly 20 advantageously allows the cuffs 100a and 100b to be separately and selectively inflated to permit the endoscope assembly 20 to sealably adjust to variations in thickness and elasticity of the body passage wall 732. The endoscope assembly 20 further advantageously allows a portion of the body passage 730 to be fluidly isolated from the remaining portion of the passage so that lavage, or any of the diagnostic procedures previously described, may be conducted in the isolated body space 720.

Figure 8:
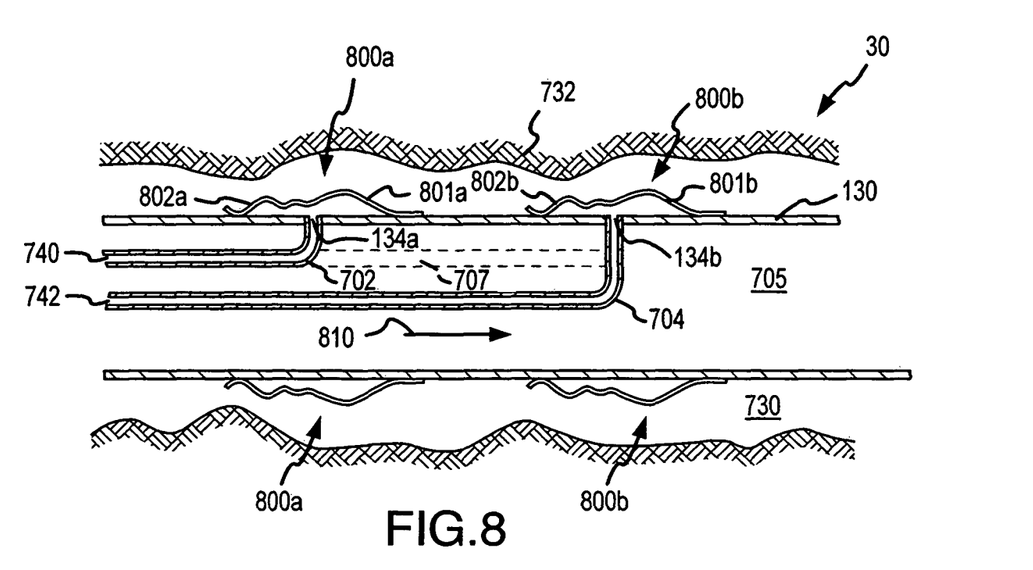
FIG. 8 is a cross-sectional view of an endoscope assembly with inflatable cuffs according to still another embodiment of the invention.

FIG. 8 is a cross-sectional view of an endoscope assembly 30 in accordance with still another alternative embodiment of the invention. The assembly 30 includes an inflatable first cuff 800a and a spaced apart inflatable second cuff 800b, which are positioned on an outer surface of a disposable sheath 130. The cuff 800a has a non-uniform wall thickness, and includes a forward portion 801a, and a rear portion 802a that has a wall thickness that is less than the wall thickness of the forward portion 801a. The cuff 800b similarly has a non-uniform wall thickness, and also includes a forward portion 801b, and a rear portion 802b that has a wall thickness that is less than the wall thickness of the forward portion 801b. The sheath 130 encloses an interior space 705, and may be positioned on an insertion tube (not shown) that is comprised of a resilient material so that the tube may be flexed as it is positioned within an internal body passage 730. Alternatively, the insertion tube may be rigid.

Inflation lumens 702 and 704 may be positioned within the interior space 705, and may be fluidly connected to a source of an inflation fluid (not shown) at lumen ends 740 and 742. The lumens 702 and 704 communicate through the sheath 130 at openings 134a and 134b to allow the inflation fluid to separately and selectively inflate the first cuff 800a and the second cuff 800b. Alternatively, a single lumen 707 (shown in FIG. 8 as a dotted line) may be used to provide inflation fluid to the first cuff 800a and the second cuff 800b so that the cuffs may be simultaneously inflated.

In operation, inflation of the first cuff 800a and the second cuff 800b through the inflation lumens 702 and 704 allows the cuffs 800a and 800b to be impressed against body passage wall 732 of a body passage 730. Further, the non-uniform wall thicknesses of the first cuff 800a and the second cuff 800b permit greater expansion of the rear portions 802a and 802b of the cuffs 800a and 800b than is obtained in the respective front portions 801a and 801b of the cuffs 800a and 800b when the cuffs 800a and 800b are inflated. The respective rear portions 802a and 802b of cuffs 800a and 800b thus develop a longitudinally-directed biasing force that acts in a direction 810 when the inflated rear portions 802a and 802b contact the body passage wall 732. In alternate embodiments, the thicknesses of the front and rear portions 801 and 802 can be reversed so that the biasing force acts in an opposite direction.

Figure 9:
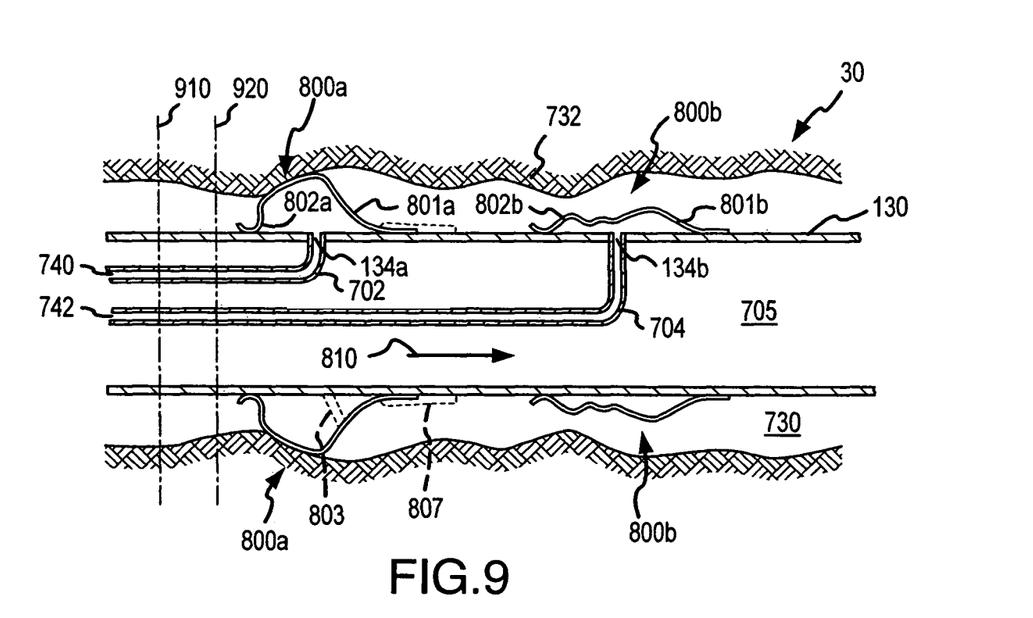
FIG. 9 is a cross-sectional view of an endoscope assembly with inflatable cuffs according to still another embodiment of the invention.

Referring now to FIG. 9, a cross-sectional view of the endoscope assembly 30 is shown with the first cuff 800a at least partially inflated, with the rear portion 802a of the cuff 800a contacting a portion of the body passage wall 732. In response to the biasing force developed by the rear portion 802a, the assembly 30 is urged along the passage 730 in the direction 810 from a first position 910 to a second position 920.

Figure 10:
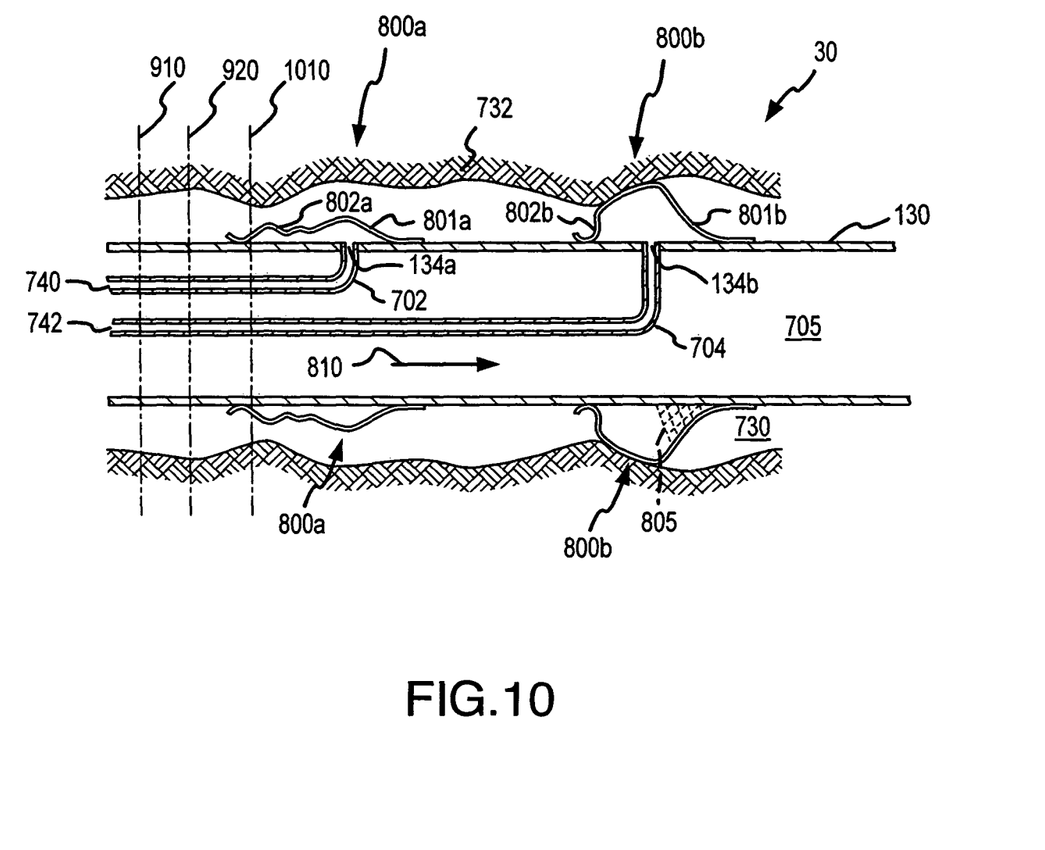
FIG. 10 is a cross-sectional view of an endoscope assembly with inflatable cuffs according to still another embodiment of the invention.

FIG. 10 is a cross sectional view of the assembly 30 with the first cuff 800a in a deflated condition, and the second cuff 800b at least partially inflated. The rear portion 802b of the cuff 800b contacts a portion of the body passage wall 732 and develops a biasing force that further urges the assembly 30 along the passage 730 in the direction 810 from the second position 920 to a third position 1010. The second cuff 800b may then be deflated, and the process repeated. By alternately inflating and deflating the cuffs 800a and 800b in the manner described, the assembly 30 is able to incrementally move along the length of the body passage 730. Alternatively, for certain body passages 730 and for certain endoscopic procedures, it may be desirable to keep one of the cuffs 800a or 800b inflated at all times (e.g. to provide an anchor), and to successively inflate and deflate the other of the cuffs to provide the desired longitudinal movement. It may also be desirable to keep one of the cuffs 800a or 800b deflated (or to eliminate one of the cuffs 800a or 800b) and to employ a single cuff to provide the desired longitudinal movement in the manner described.

Although the foregoing discussion has described the sequential alternating inflation and deflation of the first cuff 800a and the second cuff 800b, in another embodiment, the cuffs 800a and 800b may be simultaneously inflated and deflated using the single lumen 707 to move the assembly 30 along the body passage 730. Further, although the endoscope assembly 30 as depicted in FIGS. 8 through 10 has a pair of cuffs 800a and 800b, it is understood that the assembly 30 may be comprised of a plurality of inflatable cuffs located along the length of the assembly 30, and that the inflatable cuffs may be positioned along the length of the assembly 30 at varying distances. In addition, a portion of the plurality of cuffs may be oriented on the assembly 30 to apply a biasing force that urges the assembly 30 in a first direction to extend the assembly 30 into the body passage 730, while another portion of the plurality of cuffs are oriented on the assembly 30 to apply a biasing force in an opposing second direction to assist in the removal of the assembly 30 from the passage 730, as will be discussed in greater detail below, in connection with another embodiment.

It should also be understood that, although the foregoing embodiment discloses cuffs 800a and 800b having a variable wall thickness, other means may be used to obtain the differential expansion of the cuffs 800a and 800b in the manner described. For example, the composition of the material comprising the cuffs 800a and 800b may be formulated to provide the rear portions 802a and 802b with greater elasticity, so that greater expansion occurs in these portions, as opposed to the front portions 801a and 801b. Still further, internal structures, such as elastic cords 803 (FIG. 9) or elastic webs 805 (FIG. 10), for example, or other suitable structures, may be incorporated into the cuffs 800a and 800b that restrain the expansion of the front portions 801a and 801b, while permitting the corresponding rear portions 802a and 802b to freely expand.

The foregoing embodiment advantageously allows an endoscope assembly to develop a longitudinally-directed biasing force that permits the endoscope assembly to be positioned relatively deeply into a body passage, and further permits small, incremental movements of the endoscope assembly when properly positioned within the body passage. The foregoing embodiment further allows the endoscope assembly to be conveniently dislodged in situations where the assembly may become lodged in the passage.

As further shown in FIG. 9, in yet another embodiment, the assembly 30 may include one or more sleeve members 807 that partially inhibit the expansion of one or more of the cuffs 800a, 800b. In the embodiment shown in FIG. 9, the sleeve member 807 is attached to the outer surface of the sheath 130 and partially covers the first cuff 800a. As the first cuff 800a is inflated, the sleeve member 807 allows the rear portion 802a of the first cuff 800a to expand, and at least partially inhibits the expansion of the forward portion 802b. The sleeve member 807 may inhibit the expansion of the forward portion 802b by any means, including by being relatively less elastic than the first cuff 800a, or may simply add additional thickness to the forward portion 802b. Thus, the differential expansion of the cuffs 800a, 800b may be achieved, and the longitudinally-directed biasing force may be created, in an inexpensive manner by adding one or more sleeve members 807 to the assembly to achieve the beneficial results described above.

Figure 12:
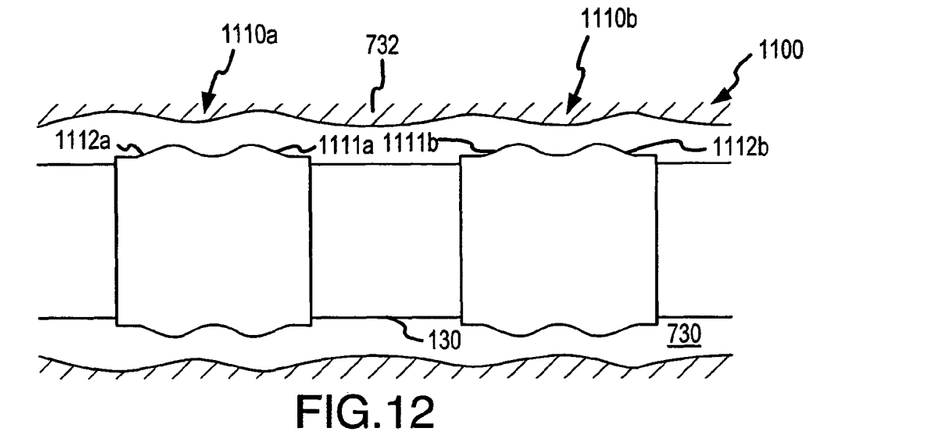
FIG. 12 is a partial side view of an endoscope assembly with inflatable cuffs according to still yet another embodiment of the invention.

FIG. 12 is a partial side view of an endoscope assembly 1100 according to still yet another embodiment of the invention. The assembly 1100 includes an inflatable first cuff 1110a and a spaced apart inflatable second cuff 1110b that are positioned on the outer surface of the sheath 130. The first cuff 1110a and the second cuff 1110b may be separately inflated, as described earlier in connection with other embodiments. As in the embodiment shown in FIGS. 8 through 10, the first cuff 1110a has a non-uniform wall thickness, which includes a forward portion 1111a, and a rear portion 1112a that has a wall thickness that is less than the wall thickness of the forward portion 1111a. The cuff 1110b also has a non-uniform wall thickness, including a forward portion 1112b and a rear portion 1111b. The forward portion 1112b has a wall thickness that is less than the wall thickness of the rear portion 1111b. The non-uniform wall thicknesses of the first cuff 1110a and the second cuff 1110b permit greater expansion of the portions 1112a and 1112b of the cuffs 1110a and 1110b than is obtained in the portions 1111a and 1111b of the cuffs 1110a and 1110b when the cuffs 1110a and 1110b are inflated. The portions 1112a and 1112b thus develop a longitudinally-directed biasing force when the inflated portions 1112a and 1112b contact the body passage wall 732.

Figure 13:
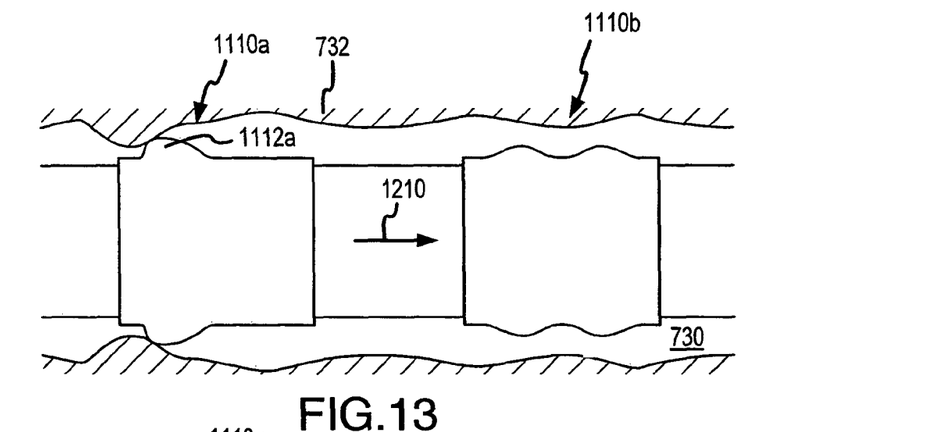
FIG. 13 is a partial side view of an endoscope assembly with inflatable cuffs according to still yet another embodiment of the invention.

Turning now to FIG. 13, a partial side view of the assembly 1100 is shown with the first cuff 1110a at least partially inflated. The rear portion 1112a of the cuff 1110a contacts the passage wall 732 and urges the assembly 1100 along the body passage 730 in a direction 1210. The cuff 1110a may be periodically inflated and deflated to move the assembly 1100 along the passage 730.

Figure 14:
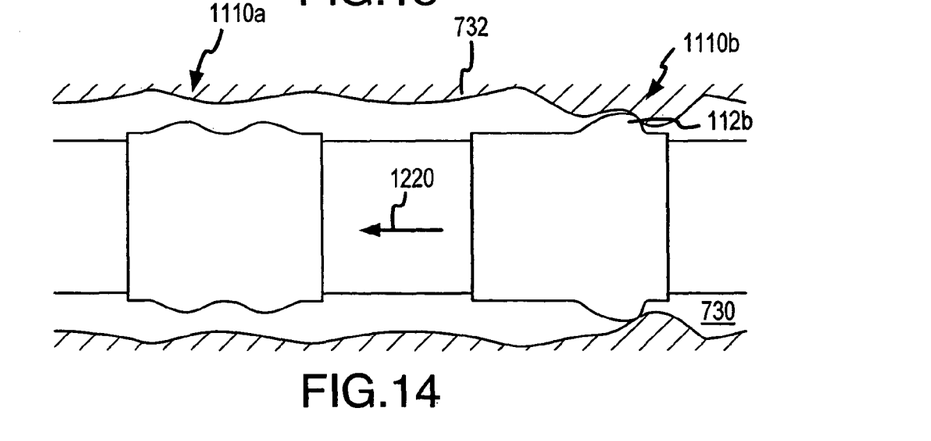
FIG. 14 is a partial side view of an endoscope assembly with inflatable cuffs according to still yet another embodiment of the invention.

Referring now to FIG. 14, a partial side view of the assembly 1100 is shown with the second cuff 1110b at least partially inflated. The front portion 1112b of the cuff 1110b contacts the passage wall 732 and urges the assembly 1100 along the body passage 730 in a direction 1220 that is opposite to the direction 1210 shown in FIG. 13.

The foregoing embodiment advantageously permits the assembly 1100 to be moved along the passage 730 in a direction that positions the assembly 1100 further into the passage 730, and also permits the assembly 1100 to be moved in the opposite direction, which may be beneficial in preventing the assembly 1100 from being lodged in the passage 730, in addition to further assisting an operator to precisely position the assembly 1100 within the passage 730.

The above description of illustrated embodiments of the invention is not intended to be exhaustive or to limit the invention to the precise form disclosed. While specific embodiments of, and examples of, the invention are described in the foregoing for illustrative purposes, various equivalent modifications are possible within the scope of the invention, as those skilled in the relevant art will recognize. Moreover, the various embodiments described above can be combined to provide further embodiments. For example, the various embodiments of the inflatable endoscope cuffs as previously described may be advantageously positioned along the length of the endoscope at uniform or varying distances to provide a plurality of inflatable cuffs along the length of the sheath. Further, different embodiments of the inflatable endoscope cuffs as previously described may be positioned at uniform or varying distances along the length of an endoscope to provide a plurality of different cuffs along the sheath to provide still further advantages. For example, the inflatable cuffs may be comprised of different materials or material thicknesses to obtain different inflation rates for the inflatable cuffs and/or different cuff volumes when the inflatable cuffs are inflated by the fluid passage. Accordingly, the invention is not limited by the disclosure, but instead the scope of the invention is to be determined entirely by the following claims.

The invention claimed is:

1. An assembly, comprising;
a sheath having a body portion adapted to at least partially encapsulate an insertion tube;
a first radially expandable flexible member sealably coupled to the body portion and defining a first inner region adapted to be inflated, the first radially expandable flexible member including a first portion capable of a first expansion when inflated, and a second portion capable of a second expansion when inflated, the first expansion being greater than the second, the first radially expandable flexible member configured to develop a longitudinally-directed biasing force when inflated and the first portion contacts a passage wall;
a second radially expandable flexible member sealably coupled to the body portion and defining a second inner region adapted to be inflated, the second radially expandable flexible member including a first portion capable of a first expansion when inflated, and a second portion capable of a. second expansion when inflated, the first expansion being greater than the second, the second expandable flexible member configured to develop a second longitudinally directed biasing force when inflated and the first portion contacts the passage wall, wherein the second longitudinally-directed biasing ibrce is in the opposing direction of the longitudinally-directed biasing force of the first radially expandable flexible member, wherein the first and second expandable flexible members are spaced apart along a length of the sheath and defining one or more isolated body spaces that extend between the members when the members are inflated within a body passage; and
at least one fluid passage coupled to the flexible members and fluidly communicating with the first inner region and second inner region.

2. The assembly according to claim 1 wherein the at least one fluid passage extends through the body portion of the sheath.

3. The assembly according to claim 1 wherein the at least one fluid passage is coupleable to a source of pressurized fluid that fluidly communicates with the inner region.

4. The assembly according to claim 1 wherein the first radially expandable flexible member comprises a circumferential member.

5. The assembly according to claim 1 wherein the first portions of the first and second radially expandable flexible members comprise a first material, and the second portions of the first and second radially expandable flexible members comprise a second material.

6. The assembly according to claim 1 wherein the first portions of the first and second radially expandable flexible members have a first elasticity, and the second portions of the first and second radially expandable flexible members have a second elasticity, the first elasticity being greater than the second. elasticity.

7. The assembly according to claim 1, further comprising an insertion tube, the body portion of (he sheath at least partially encapsulating the insertion tube.

8. The assembly of claim 1. further comprising a second fluid passage in fluid communication with the one or more isolated body spaces.

9. The assembly of claim 1 wherein the flexible members each comprise a resilient material.

10. The assembly of claim 1 wherein the at least one first fluid passage comprises a first lumen extending from a first opening in the sheath that communicates with a first annular space, and a second lumen that extends from a second opening that communicates with a second annular space.

11. A method of forming an e endoscope assembly, comprising:
providing a. sheath having a body portion adapted to at least partially encapsulate an insertion tube;
forming a first radially expandable flexible circumferential member sealably coupled to the body portion and defining a first annular inner region adapted to be inflated, the first radially expandable flexible circumferential member being formed by forming a flexible member having a first portion with a first elasticity and a second portion with a second elasticity, the first elasticity being different from the second elasticity, the at least one radially expandable flexible member configured to develop a longitudinally-directed biasing force when inflated and the first portion contacts a passage wall;
forming a second radially expandable flexible circumferential member sealably coupled to the body portion and defining a second annular inner region adapted to be inflated, the second radially expandable flexible circumferential member being formed by forming a flexible member having a first portion with a first elasticity and a second portion with a second elasticity, the first elasticity being, different from the second elasticity, the second radially expandable flexible member configured to develop a second longitudinally-directed biasing force when inflated and the first portion contacts the passage wall, wherein the second longitudinally-directed biasing force is in the opposing direction of the longitudinally-directed biasing force of the first radially expandable flexible member, wherein the first and second radially expandable flexible circumferential members are formed apart along a length of the sheath and defining one or more isolated body spaces that extend between the members when the members are inflated within a body passage; and
providing at least one fluid passage coupled to the flexible members and fluidly communicating with the first and second annular inner regions.

12. The method according to claim 11 wherein providing at least one fluid passage comprises providing at least one fluid passage extending through the body portion of the sheath.

* * * * *